United States Patent
Warlick et al.

(10) Patent No.: US 8,057,411 B2
(45) Date of Patent: Nov. 15, 2011

(54) WOUND CARE VACUUM BANDAGING IN COMBINATION WITH ACOUSTIC SHOCK WAVE APPLICATIONS

(75) Inventors: John Warlick, Woodstock, GA (US); Michael F Rozmajzl, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 1238 days.

(21) Appl. No.: 11/739,715

(22) Filed: Apr. 25, 2007

(65) Prior Publication Data

US 2008/0269651 A1    Oct. 30, 2008

(51) Int. Cl.
*A61H 7/00* (2006.01)
(52) U.S. Cl. .............. 601/6; 601/9; 601/11; 602/43; 602/48
(58) Field of Classification Search .......... 601/2, 6, 601/7, 9, 10, 11, 46, 47, 48, 84; 602/41, 602/42, 43, 46, 48; 604/289, 304, 305, 307, 604/308, 313–316
See application file for complete search history.

(56) References Cited

U.S. PATENT DOCUMENTS

| 4,382,441 A | 5/1983 | Svedman |
| 6,068,596 A | 5/2000 | Weth et al. |
| 6,398,767 B1 * | 6/2002 | Fleischmann ............ 604/304 |
| 2003/0129154 A1 | 7/2003 | McDaniel |
| 2007/0021698 A1 | 1/2007 | Fleischmann |
| 2007/0239078 A1 * | 10/2007 | Jaeb ...................... 601/2 |

FOREIGN PATENT DOCUMENTS

DE    4012232    10/1991

* cited by examiner

*Primary Examiner* — Quang D Thanh
(74) *Attorney, Agent, or Firm* — David L King

(57) ABSTRACT

A method and device for treating wounds 10 of tissue 11 is disclosed. The method has the steps of applying a porous pad 12 upon the treatment surface of the tissue 11; covering the treatment surface and the porous pad 12 with a foil or sealing cover 14 for isolating the treatment surface and the porous pad 12 from the atmosphere; filling the volume under the foil or sealing cover 14 with fluid 100 and purging air from the volume under the foil or sealing cover 14 thereby fluid 100 saturating said porous pad 12: applying an acoustic shock wave treatment through the foil or sealing cover 14 or surrounding tissue 11 or a combination thereof sending acoustic shock waves 200 through the volume to the treatment surface and underlying tissue 11 and thereafter pulling a vacuum to create a sub-atmospheric pressure under the foil or sealing cover 14 wherein the combination of the applied acoustic shock waves 200 and sub-atmospheric conditions stimulates healing of the treatment surface and underlying tissue 11. Preferably the acoustic shock waves 200 are unfocused or a wide area focused shock wave pattern. More preferably the shock waves 200 are sufficiently low energy or amplitude to avoid the sensation of pain during the treatment process thereby eliminating the need for anesthesia or localized numbing of the treatment area.

12 Claims, 4 Drawing Sheets

WOUND CARE VACUUM BANDAGING IN COMBINATION WITH ACOUSTIC SHOCK WAVE APPLICATIONS

TECHNICAL FIELD

The invention concerns an improved process and device for wounds using a combination of a vacuum bandage and acoustic shock waves.

BACKGROUND OF THE INVENTION

The treatment of deep wounds historically involved salves, solutions or solid medicament carriers in impregnated wound coverings. These treatments at best were ineffective and often due to the toxic secretions emanating deep in the wound resulted in further tissue damage or injurious reactions and infections.

Vacuum bandages over a wound were disclosed in German patent DE 4012232 A1 wherein the wound is covered by a thin semi-permeable foil. A supply line and a removal line are provided under the foil in the wound area. Active substances can be applied to the wound surface under the foil via the supply line by means of a syringe. After the desired application period the active substances can, in certain cases together with the wound secretion, be suctioned out via the removal line by means of a vacuum source. The supply line is provided with a self-acting closing safety valve, which is opened by the introduced syringe for introduction of the fluid active substances. Likewise there is provided on the removal line a closure or blockage mechanism, which closes off the output side during the application period of the active substance.

In this known installation bandage the active substances are applied directly upon the wound surface and suctioned off from the wound surface. The active substance can thus only be applied in imprecise doses and in particular in the case of large wound surface areas an even effect upon the entire surface is difficult to achieve. A long time continuous effect can not realized.

From U.S. Pat. No. 4,382,441 it is known, for treatment of wound surfaces, to lay a padding or dressing made of a porous material upon the wound surface and to sealingly cover this. The active substance to be applied is continuously conveyed through the padding, for which a fluid supply connection and a fluid removal connection communicate with the padding. The capillary effect of the porous padding optimizes the distribution of the supplied active substance over the entirety of the surface of the padding in contact with the wound surface.

The porous padding is substantially form-stable and also the sealing cover is preferably form-stable. The fluid active substance is conveyed through the padding in a continuous stream, whereby a stream distribution results, in which the fluid active substance flows essentially along the area between the fluid supply connection and fluid removal connection, while the edge areas of the padding are barely perfused. Thus, in these edge areas the active substances are only exchanged in small amounts and, further, in the edge areas accumulations of wound secretion are only insufficiently removed. Beyond this the relatively form stable padding does not lie in all areas equally against the wound surface, so that also hereby an even application of the active substance and an even removal of the wound secretion is compromised. A continuous effect is not envisioned or intended.

A solution to the above mentioned deficiencies in deep wound treatments was proposed in US patent application 2007/0021698 A1, the summary of which is repeated as follows. The invention was concerned with the task, of providing a process and device for application of active substances to a wound surface, which guarantees a high effectiveness of the applied active substance over the entire wound surface, makes possible an optimal dosing of the active substance, and enhances the wound healing process.

The basic idea of the invention was to lay a padding or bandage of an elastic compressible porous material upon the wound surface and to cover the wound surface and the padding with a sealing layer or foil, which closes off the wound and the padding against the atmosphere. The supply line and the removal line are respectively provided with controllable closure devices which at the appropriate time are so controlled, that the introduction of the active substance and the suctioning off of the active substance and in certain cases the wound secretion are separated from each other in time. Between the time interval in which the closure device of the supply line is opened and the active substance is supplied, and the point in time, in which the closure device of the removal line is opened in order to suction out the active substance and the wound secretion, there is programmed or provided an treatment dwell time interval, in which both closure devices are closed and the active substance statically has an effect upon the wound surface. After the suctioning off of the active substance and the wound secretion there was, besides this, a time interval programmed in which the closure mechanism of the supply side remains closed and a vacuum is maintained in the area of the wound. For this the closure mechanism of the suctioning side can remain open, so that via the vacuum source a constant vacuum is maintained in area of the wound and the wound secretion is suctioned off. The closure mechanism of the removal side can also be closed, so that the vacuum produced initially can be maintained. It is also possible in this phase that the closure mechanism of the removal side is temporarily controlled to be open, in order that the vacuum is reestablished, in case this drops below a pre-determined value.

The dwell time interval, in which the padding is impregnated or soaked with the active substance and the active substance was applied with a continuous effect upon the wound surface, was selected corresponding to the nature of the active substance, its dosing and the indications given by the condition of the wound surface. In the vacuum time interval, in which no active substance is applied and only the wound secretion is suctioned off, the bodily immunological repair and immune processes of the tissue can proceed unhindered, so that the wound healing is optimized. Thus, active treatment phases and healing phases alternate temporally one after the another. In the treatment phase the wound system is actively engaged by means of the active substances, such as for example antibiotics or antiseptics, in order to fight or combat infections and the like. Since such active substances as a rule besides the desired main effect also have undesired side effects, the active substances are suctioned off subsequent to the active treatment phase and with them the wound secretion, which contains the decomposition products produced during the active treatment phase with their, in certain cases, toxic agents. In the subsequent vacuum time interval the body's own immunological healing process can proceed optimally, without being compromised by the undesired side effects of the active substances and the decomposition products produced during the combating of the wound infection.

Preferably the closure mechanisms of the supply line and removal line are temporally so controlled, that the introduction of the active substance begins slowly and with a minimal volumetric stream. Thereby it is prevented, that wound pain is caused or increased by a too-sudden and rapid introduction of active substance. Likewise, the opening of the closure mechanism of the removal line is temporally controlled in such a manner, that the vacuum increases only gradually. A too rapid, sudden vacuum leads likewise to substantially wound pain.

The padding provided upon the wound surface is comprised of an elastic compressible porous material, preferably a PVA-sponge (polyvinyl alcohol-sponge), wherein a flexible foil is employed for covering. If a vacuum is produced in the foil-covered wound area, then the foil lies tightly upon the wound and compresses the padding. Thereby the padding lies over its entire surface equally tightly on the wound surface. This improves the suctioning off of the wound secretion during the vacuum time interval. Should the inlet opening be opened for introduction of the active substance, then the porous padding suctions the active substance in, whereby it expands on the basis of its elastic resilience. Thereby it is achieved, that the padding evenly absorbs the active substance in the manner of a sponge. The active substance is evenly distributed over the entire surface of the padding and acts upon the entire wound surface in an even manner. This is improved thereby, that the padding in the vacuum phase lies tightly against the wound surface. The even distribution of the active substance over the entire surface is not impeded or hindered during the active treatment phase, since after the end of the introduction, during the active treatment time interval, a static condition exists, in which the introduction and removal lines are closed.

Since the wound treatment can extend over a longer period of time, for example over several days, it can occur, that in particular during a longer vacuum phase the pores of the padding slightly adhere or become glued together. Such adhesion increases the resistance against the introduction of active substance. Thereby the introduction of the active substance by gravity can be impeded. In such a case it is purposeful, at the beginning of the introduction of the active substance, to first rinse the porous padding clean. For this, at the beginning of the introduction of the active substance, first a small volume of a fluid active substance is introduced under pressure, in order to rinse through the pores of the padding and to dissolve adhered areas. The introduction under pressure can advantageously be achieved by a syringe, which is connected to the inlet. Via piston pressure of the syringe a first dose of active substance can be employed for rinsing under pressure, before the introduction of the active substance occurs by gravity. In certain cases it is also possible, that the amount of the fluid active substance necessary for the entire introduction period is supplied by means of the syringe.

The process and vacuum wound covering device as described therein US application 2007/0021689 is incorporated herein by reference in its entirety. The use of this form of device provides a unique and heretofore unused opportunity for more rapidly initiating the healing process in such difficult large and deep wounds.

Historically vacuum bandages employed a sponge which by its cellular open pore nature exhibited numerous air pockets.

Applicants of the present invention have developed a new family of unfocused or wide area unfocused acoustic shock waves that can transmit wave patterns with either a wide area focal region or with no focal point or a focal point lying outside the wound area, preferably external of the patient's body. The acoustic wave patterns provide both a germicidal effect on the tissue upon which they impinge, and also are known to accelerate healing. These wave patterns are best transmitted through a fluid gel to the applicator head and the patient's skin directly. With covered wounds as described above, transmission through the bandage was considered impossible due to the residual air pockets and therefore the use of such shock waves was not contemplated as complimentary to vacuum wound treatments.

A subtle heretofore unappreciated, but remarkably simple adjustment of the use of such vacuum bandage devices as described in the prior art provides the basis for the present invention.

SUMMARY OF THE INVENTION

A method and device for treating wounds of tissue is disclosed. The method has the steps of applying a porous pad upon the treatment surface of the tissue; covering the treatment surface and the porous pad with a foil or sealing cover for isolating the treatment surface and the porous pad from the atmosphere; filling the volume under the foil or sealing cover with fluid and purging air from the volume under the foil or sealing cover thereby fluid saturating said porous pad: applying an acoustic shock wave treatment through the foil or sealing cover or surrounding tissue or a combination thereof sending acoustic shock waves through the volume to the treatment surface and underlying tissue and thereafter pulling a vacuum to create a sub-atmospheric pressure under the foil or sealing cover wherein the combination of the applied acoustic shock waves and sub-atmospheric conditions stimulates healing of the treatment surface and underlying tissue. Preferably the acoustic shock waves are unfocused or a wide area focused shock wave pattern. More preferably the shock waves are sufficiently low energy or amplitude to avoid the sensation of pain during the treatment process thereby eliminating the need for anesthesia or localized numbing of the treatment area. By using acoustic shock waves the treatment of the shock waves creates a germicidal effect on the porous pad and the treatment surface of the tissue and a fluid drain system provided within the volume under the foil or sealing cover can remove tissue toxin and other contamination products during a fluid purging process thereafter the drainage vacuum can be applied to the entire volume under the sealing cover to provide continual drainage of body fluid and secretions that are created in the areas of the damaged tissue. This greatly improves the healing process of the tissue and reduces the chances for infection, furthermore to further reduce the chances of infection the step of introducing a medicament, antiseptic or antibiotic into the volume under the sealed cover prior to activation of the shock waves can be used to stimulate absorption or covering of the treatment surface tissue during and after the shock wave treatment.

To achieve the desired treatment, the vacuum treatment device adapted for transmission of acoustic shock waves is described. The vacuum treatment device for application to tissue has a porous pad for applications upon a treatment surface of the tissue. An air tight, but water vapor permeable foil or sealing cover for covering the treatment surface and the porous padding which seals and isolates the treatment surface from air. At least one fluid supply line for supplying fluid to the treatment surface and the porous pad; at least one fluid removal line for removing the fluid from the treatment surface and the porous padding, the removal line being connected to a vacuum source where the introduction of fluids through the supply line in combination with removal of fluids and entrapped air through the removal line, thereby fluid saturates the porous pad and treatment surface and wherein the fluid saturated volume under the foil or sealing cover enables an acoustic shock wave applicator head to be acoustically coupled to the foil or sealing cover, the foil or sealing cover and adjacent tissues, or the adjacent tissues for the transmission of acoustic shock waves to the treatment surface through the fluid saturated porous pad.

Preferably the acoustic shock wave device transmits either convergent, divergent, near planar or otherwise unfocused shock waves to the treatment surface and underlying tissue or alternatively wide area focused acoustic shock waves to the treatment and underlying tissue in such a condition that makes it unnecessary to administer additional anesthesia or numbing of the tissue prior to the application of the acoustic shock waves.

The padding is preferably made of an elastic compressible porous material, preferably a pored PVA foam material.

In addition to the above the preferred device also includes a controller, a supply side valve, a return side valve and a supply side fluid pressure infusion pump wherein the controller can actuate the supply side valve, the return side valve, the vacuum or the pressure infusion pump to provide the fluid filled infusion of said porous pad or the drainage of said porous pad and treatment surface or a combination thereof for simultaneous fluid infusion and vacuum drainage. After a fluid infusion, the return side is either closed or restricted and there is created a fluid filled reservoir or volume directly under the foil or sealing cover void of air. When this area is completely purged of air it is possible to transmit acoustic shock wave treatments through the foil or sealing cover, the tissue adjacent the foil or sealing cover, or a combination of the two passing through the fluid saturated pad to the treatment tissue and underlying treatment surface. The return side can be closed and a vacuum source applied to create a sub-atmospheric pressure to the treatment tissue which in combination with the acoustic shock waves to stimulate the tissue. Furthermore medications can be applied to the porous pad and upon such application the transmission of acoustic shock waves will increase the ability of the treatment surface area to absorb such medications thereby effectively providing a better medicant coverage than otherwise would be achieved. These devices being effectively germicidally treated by the acoustic shock waves can remain on the patient without changing the bandage or dressing nearly as often as is normally required. The removal of the bandages often times creates additional trauma to the wound area causing the entire area to require additional healing as the wound or treatment area is being cleaned and re-bandaged. The use of acoustic shock waves limits the number of times this is necessary and therefore provides a better opportunity to provide a healing for the patient.

DEFINITIONS

"apoptosis" is the biological process of controlled, programmed cell death, by means of which cells die by a process of condensation without the release of cell contents into the surrounding milieu.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"cytoplasm" The part of a cell that contains the CYTOSOL and small structures excluding the CELL NUCLEUS; MITOCHONDRIA; and large VACUOLES.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"extracorporeal" occurring or based outside the living body.

A "generalized paraboloid" according to the present invention is also a three-dimensional bowl. In two dimensions (in Cartesian coordinates, x and y) the formula $y^n = 2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"lactate dehydrogenase (LDH)" A tetrameric enzyme that, along with the coenzyme NAD+, catalyzes the interconversion of lactate and pyruvate. In vertebrates, genes for three different subunits (LDH-A, LDH-B and LDH-C) exist.

"mitochondria" Semiautonomous, self-reproducing organelles that occur in the cytoplasm of all cells of most, but not all, eukaryotes. Each mitochondrion is surrounded by a double limiting membrane. The inner membrane is highly invaginated, and its projections are called cristae. Mitochondria are the sites of the reactions of oxidative phosphorylation, which result in the formation of ATP. They contain distinctive RIBOSOMES, transfer RNAs (RNA, TRANSFER); AMINO ACYL T RNA SYNTHETASES; and elongation and termination factors. Mitochondria depend upon genes within the nucleus of the cells in which they reside for many essential messenger RNAs (RNA, MESSENGER). Mitochondria are believed to have arisen from aerobic bacteria that established a symbiotic relationship with primitive protoeukaryotes.

"necrosis" A pathological process caused by the progressive degradative action of enzymes that is generally associated with severe cellular trauma. It is characterized by mitochondrial swelling, nuclear flocculation, uncontrolled cell lysis, and ultimately CELL DEATH.

A "paraboloid" according to the present invention is a three-dimensional reflecting bowl. In two dimensions (in Cartesian coordinates, x and y) the formula $y^2 = 2px$, wherein p/2 is the distance of the focal point of the paraboloid from its apex, defines the paraboloid. Rotation of the two-dimensional figure defined by this formula around its longitudinal axis generates a defacto paraboloid.

"phagocytosis" The engulfing of microorganisms, other cells, and foreign particles by phagocytic cells.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100's of ns. The duration of a shock wave is typically below 1-3 micro-seconds (μs) for the positive part of a cycle and typically above some micro-seconds for the negative part of a cycle.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

The present invention as described below employs a vacuum wound bandage device 1, 1A in combination with an acoustic shock wave applicator device.

The vacuum wound bandage device 1, 1A can be of any particular size or shape but unlike conventional bandaging, the vacuum wound bandaging device 1 must be designed to easily transmit acoustic shock waves.

Prior to the present invention all such devices notoriously had a sponge or otherwise porous pads filled with entrapped air. Those skilled in the art of acoustic shock wave therapies recognized that such bandaging would act as a sound wave absorber or dampener, making it virtually impossible to use shock waves to treat such covered wounds.

Furthermore, severely damaged tissue 11 in these deep wounds, if exposed to focused high energy shock waves caused additional hemorrhaging and a strong sensation of pain, thus making the use of conventional acoustic shock waves as a treatment unacceptable to the patient and the attending physician.

This basically led to a complete belief that a combination was totally incompatible and unworkable by those skilled in the art of treating such sever wounds.

In US publication 2007/0021698 A1 published Jan. 25, 2007 a vacuum bandage is disclosed entitled "Process and Device for Application of Active Substances to a Wound Surface" the description of which is incorporated herein by reference in its entirety herein. In this application the primary function is to provide a device which facilitates the use of medications, antiseptics and or antibodies to the covered wound via a supply line and wherein the wound can be exposed to sub-atmospheric pressure to stimulate healing.

Figure 1:
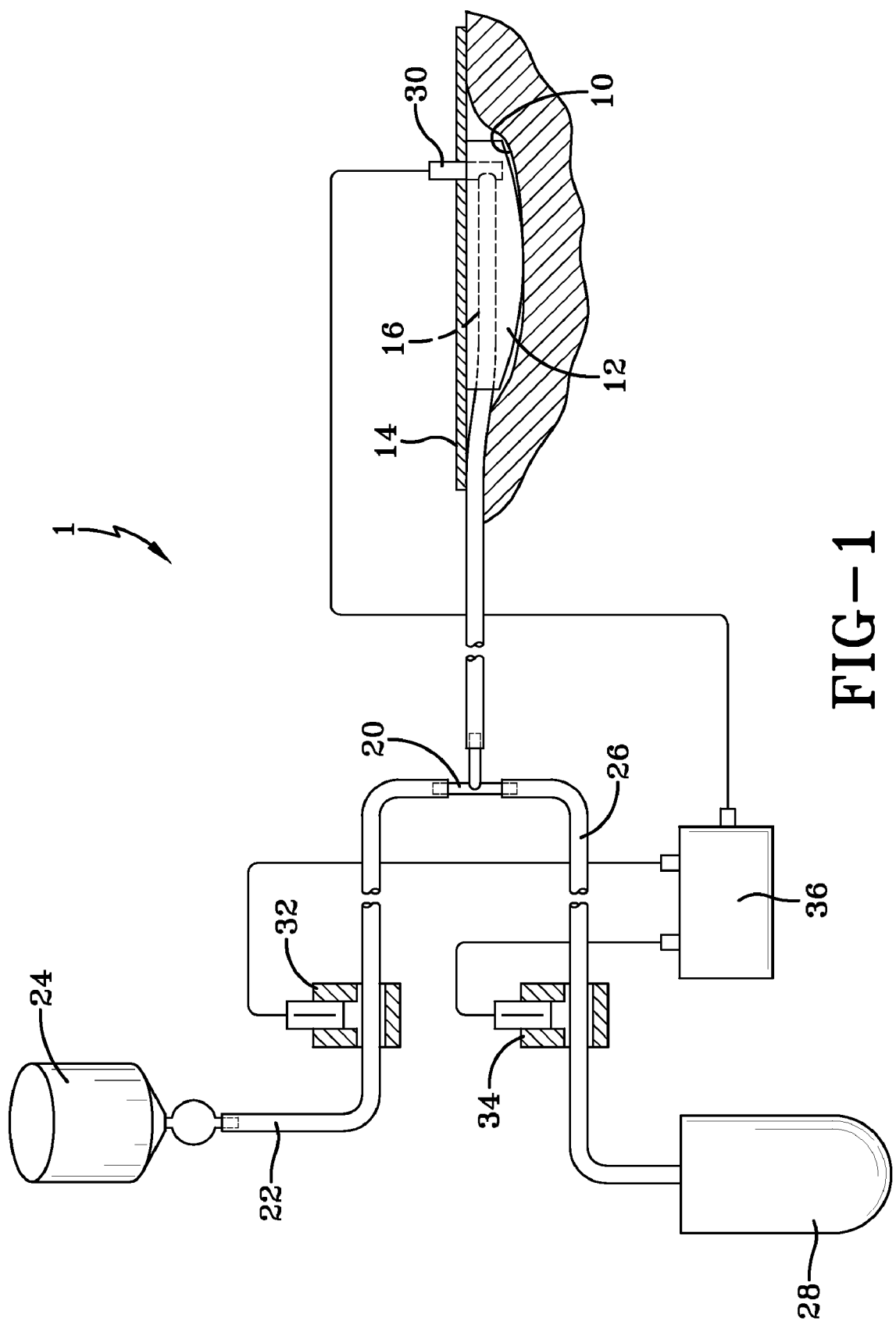
FIG. 1 is an exemplary embodiment of the device according to the invention, to which an acoustic shock wave applicator head can be coupled directly to the outer covering of the device.
Figure 2:
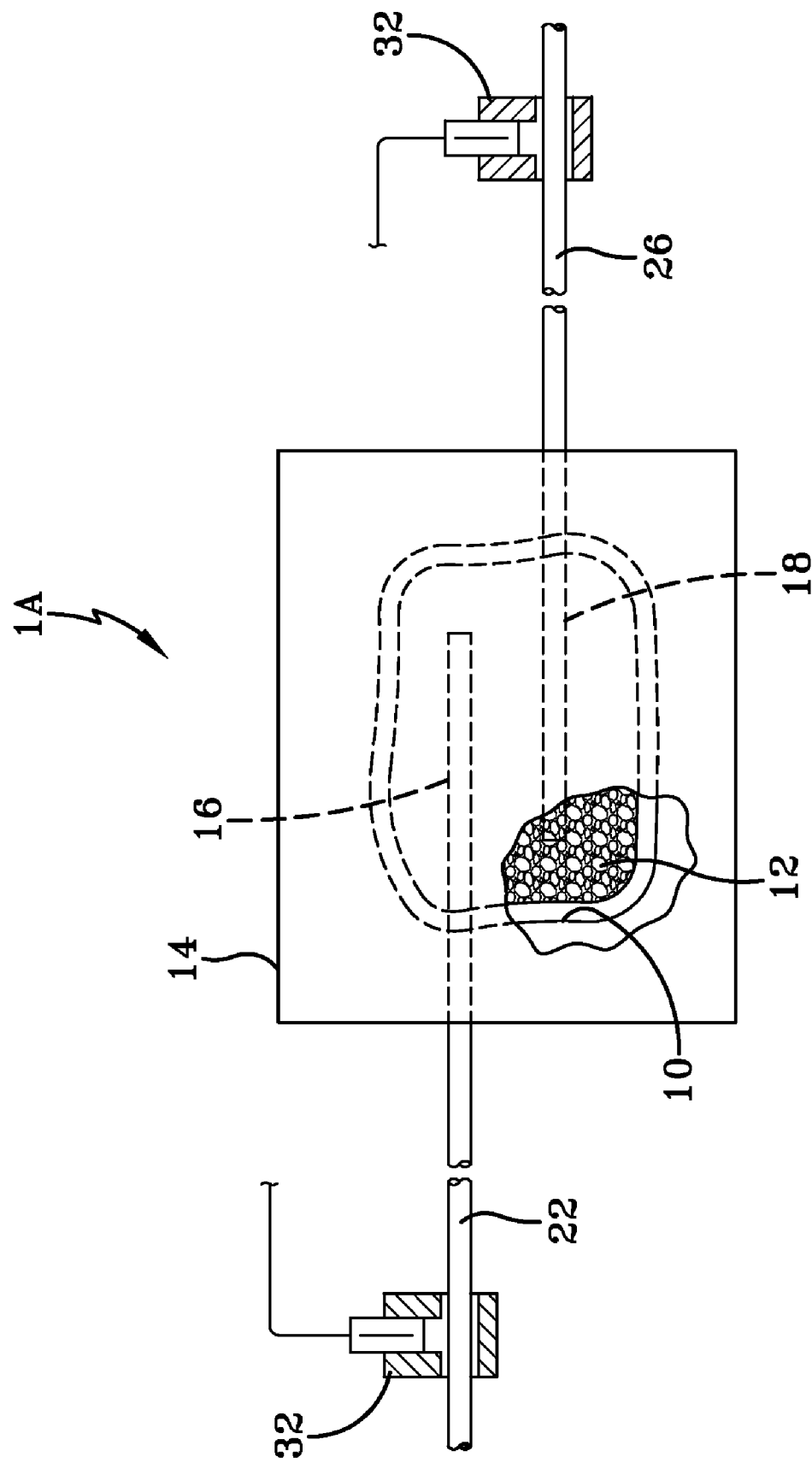
FIG. 2 is a modification of the device of FIG. 1 showing independent supply line and drainage line, as shown in a top view.

FIGS. 1 and 2 show a vacuum wound bandage device 1, 1A respectively which is described as follows.

For treatment of a large surface area deep wound 10 a padding 12 is applied. The padding 12 is comprised of a porous elastic compressible material, preferably of an open pored PVA foam material. The padding 12 is cut or trimmed to correspond to the contour of the wound 10. The wound 10 and the padding 12 are covered over by a foil 14 and sealingly closed off. The foil 14 is so cut, that it covers over the padding 12 and the wound 10 and extends beyond the edges of the wound. The foil 14 is sealingly secured to the skin surface about the wound circumference, for example, it is adhered.

The foil 14 is flexible and is comprised of a synthetic or plastic material, which permits the diffusion of water vapor, however, provides an air-tight enclosure.

In the padding 12 there is introduced a drainage tube 16, a so-called Redon-tube, which is perforated in the end area lying in the padding 12. The not perforated area of the drainage tube 16 is covered over by the foil 14 and extends out therefrom.

In the illustrative embodiment of FIG. 1 there is introduced in the proximal end of the drainage tube 16 a T-shaped branch or manifold piece 20. On its one connection of the manifold 20 a hose is attached as supply side 22, which leads to a known infusion container 24. On the other connection of the manifold 20 a hose is attached as removal 26 which leads to a receptacle container 28 onto which, via a connection line 30, a vacuum source is connectable. Such a receptacle container 28 is likewise known per se.

The supply line 22 has associated therewith a closure mechanism 32 and the removal line 26 has a closure mechanism 34 associated therewith. The closure mechanisms 32 and 34 are continuously adjustable between a closed position and an open position and are operated via a controller 36.

In the here shown illustrative embodiments the closure mechanisms 32 and 34 are respectively constructed as hose clamps, which include a receptacle, in which the hose of the supply line 22 or, as the case may be, the removal line 26, can be introduced. A plunger is, as indicated by arrows in the figure, controlled electromagnetically, pneumatically, hydraulically or in an otherwise known manner by the controller 36, in order that the introduced hose is pressed against a side wall and with squeezing is closed off or in order that the cross-sectional area of the hose is continuously unimpeded.

In certain cases a pressure sensor 38 can be introduced in the wound area under the foil 14, which senses the pressure existing under the foil 14 and reports this to the controller 36.

In the infusion container 24 a fluid active substance is pre-supplied, which can be introduced to the padding 12 and therewith to the wound surface via the supply line 22 and the drainage hose 16 in the case of opened closure mechanism 32 and closed closure mechanism 34. In the case of the closed closure mechanism 32 and opened closure mechanism 34 the active substance and the wound secretion produced in the wound 10 can be suctioned off via the removal line 26 into the receptacle container 28.

FIG. 2 shows a variation of the device 1A, which in comparison to the illustrative embodiment of FIG. 1 differs therein, that the padding 12 introduced in the wound 10 has introduced therein two hoses 16 and 18. The hose 16 is connected with the supply line 22, while the drainage hose 18 is connected with the removal line 26. A branching is thus unnecessary.

In the illustrative embodiment according to FIG. 1 the hose 16 forms a hose dead-end, in which on the one hand the active substance can be introduced and out of which on the other hand the active substance can be suctioned out. Thereby during the introduction of the fluid active substance gas bubbles can be trapped in the drainage hose 16, which would interfere with the introduction of the active substance. This difficulty cannot occur in the embodiment according to FIG. 2, since any gas bubbles trapped in the hose 16 would be suctioned out via the drainage hose 18. The embodiment according to FIG. 1 however has the advantage, that only one hose must be introduced under seal under the foil 14.

A particular advantageous feature of the exemplary vacuum wound device is the closure mechanisms 32 and 34 are controlled by the controller 36 to be closed and in the wound there exists a vacuum of approximately 10 to 80 kPa. On the basis of this vacuum the foil or sealing cover 14 is pressed against the wound surface, wherein the elastic padding 12 is compromised. The controller 36 directs the closure mechanism 32 to open, so that the fluid 100 can flow out of the infusion container 24 via the supply line 22 and the hose 16 into the padding 12. During the inflow the padding 12 suctions itself to fullness with fluid 100, whereby it expands on the basis of its elastic spring resilience. The porous padding 12 is suctioned full of fluid 100, whereby under the foil 14 a certain over-pressurization exists, which is preferably determined by the height of the infusion container 24 with respect to the wound 10. In certain cases a pressure controlled pump can be introduced in the supply line 22 controlled by the pressure sensor 38.

The opening of the closure mechanism 32 of the supply line 22 in the introduction time interval T1 is controlled by means of the controller 36 in such a timed manner, that the volumetric flow of the fluid active substance only increases slowly. A sudden opening of the closure mechanism 32 would result in a very rapid influx of the active substance. This can result in wound pain to the patient, in particular since the fluid active substance as a rule does not correspond to the body temperature of the patient.

During the vacuum phase in certain circumstances the pores of the compromised padding 12 can adhere or stick together. Such an adhesion prevents the influx of the active substance under only gravity, which is determined by the height of the infusion container 24 with respect to the wound 10. Such a possible adhesion of the pores can be rinsed clean thereby that during the opening of the closure mechanism 32 first a certain volume of the fluid active substance is introduced under pressure. For this a suitable volume of the active substance can be introduced by means of a piston syringe via the supply line 22. The piston syringe is therefore preferably connected to the supply line 22, for which for example a three-way cock or valve can be associated with the supply line 22, onto which the piston syringe is connected.

As soon as the padding 12 has suction-filled itself with fluid active substance, the closure mechanism 32 of the supply side 22 is closed at time T2. For a treatment dwell time interval T2 the closure mechanisms 32 and 34 of the supply line 22 and the removal line 26 remain closed, so that the active substance contained in the padding 12 can act upon the surface of the wound 10. The duration of the treatment dwell time interval T2 can be predetermined by the controller 36 and is based upon the type and condition of the wound 10 and according to the type and concentration of the active substance. When the active substance during the time interval T2 has had a sufficient effect or action upon the wound surface, then at time T3 the closure mechanism 34 of the removal line 26 is opened. Thereby via the vacuum existing through the connection line 30 the fluid active substance is suctioned out of the padding 12 and the wound 10 via the hose 16 (in FIG. 1) or as the case may be the drainage hose 18 (in FIG. 2). At the same time the wound fluid 100 or secretion is suctioned out, which has accumulated in the wound 10 in the treatment dwell time interval T2 and which contains decomposition and breakdown products produced through the action of the active substance.

The opening of the closure mechanism 34 is timely so controlled by the controller 36, that the flow-through cross-section of the removal line 26 opens only slowly and the vacuum in the padding 12 and the wound 10 only increases gradually, through the continuous line. An immediate and complete opening of the closure mechanism 34 would lead to a very rapid pressure drop in the area of the wound, which would be associated with wound pains for the patient.

Should at time T4 the original vacuum again be achieved, which in certain cases can be monitored by the pressure sensor 38, so the fluid active substance can again be completely removed from the wound 10 and the padding 12. The vacuum is then maintained for a vacuum time interval T4. Thereby as a rule the closure mechanism 34 remains open, so that the vacuum is continuously maintained by the vacuum source 30, and the produced wound secretion is continuously suctioned off into the receptacle retainer 28. It is also possible, that the closure mechanism 34 is closed or temporarily closed and only opened for short period of times when the vacuum monitored by pressure sensor 38 must be regenerated.

All of this is fully described in US patent publication US 2007/0021689, which has been incorporated herein by reference in its entirety.

Figure 3:
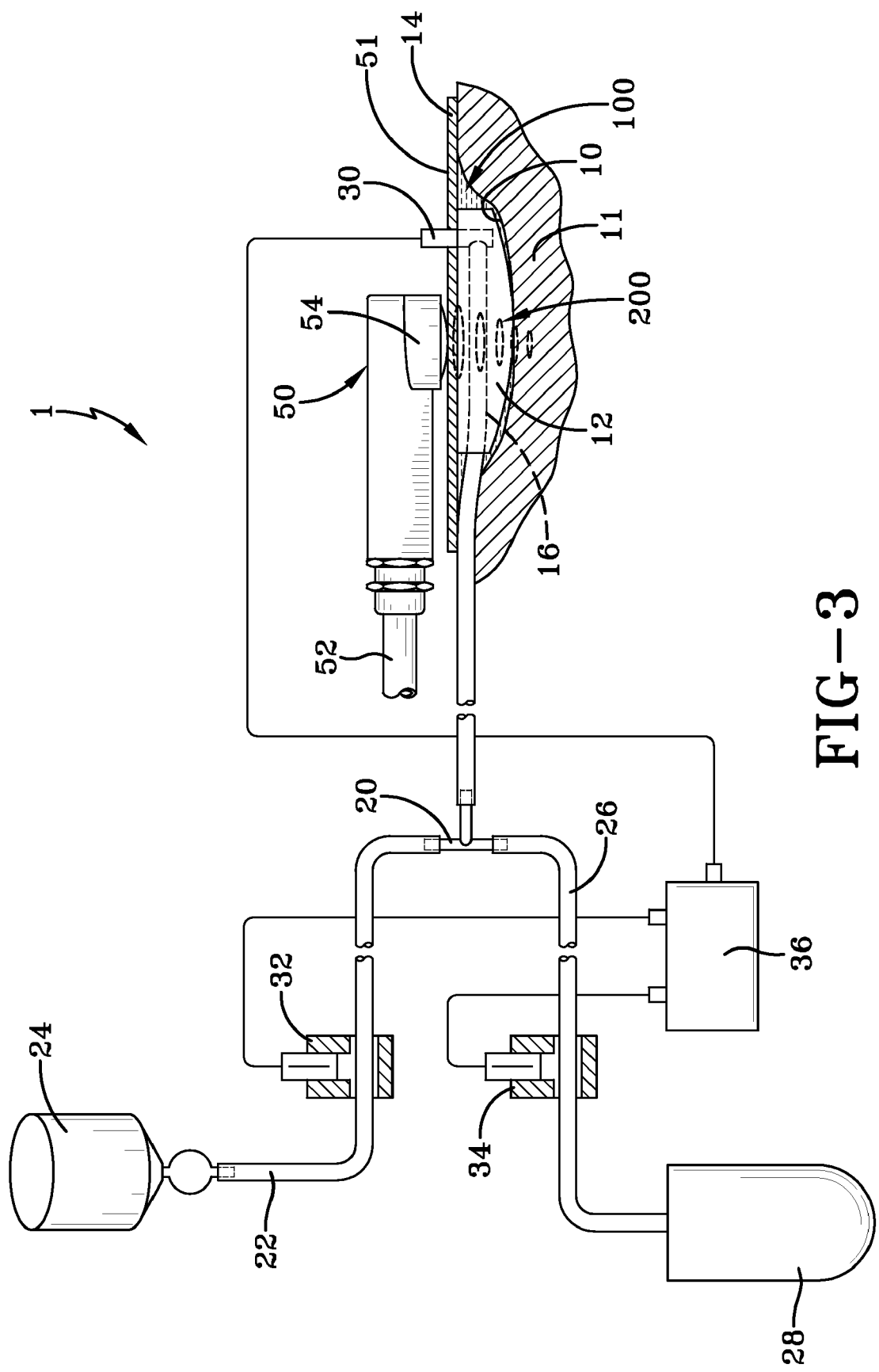
FIG. 3 shows the exemplary device of FIG. 1 being used in combination with a shock wave applicator; the applicator head is illustrated showing how the acoustic shock waves penetrate through the sealing cover into the underlying tissue area.
Figure 4:
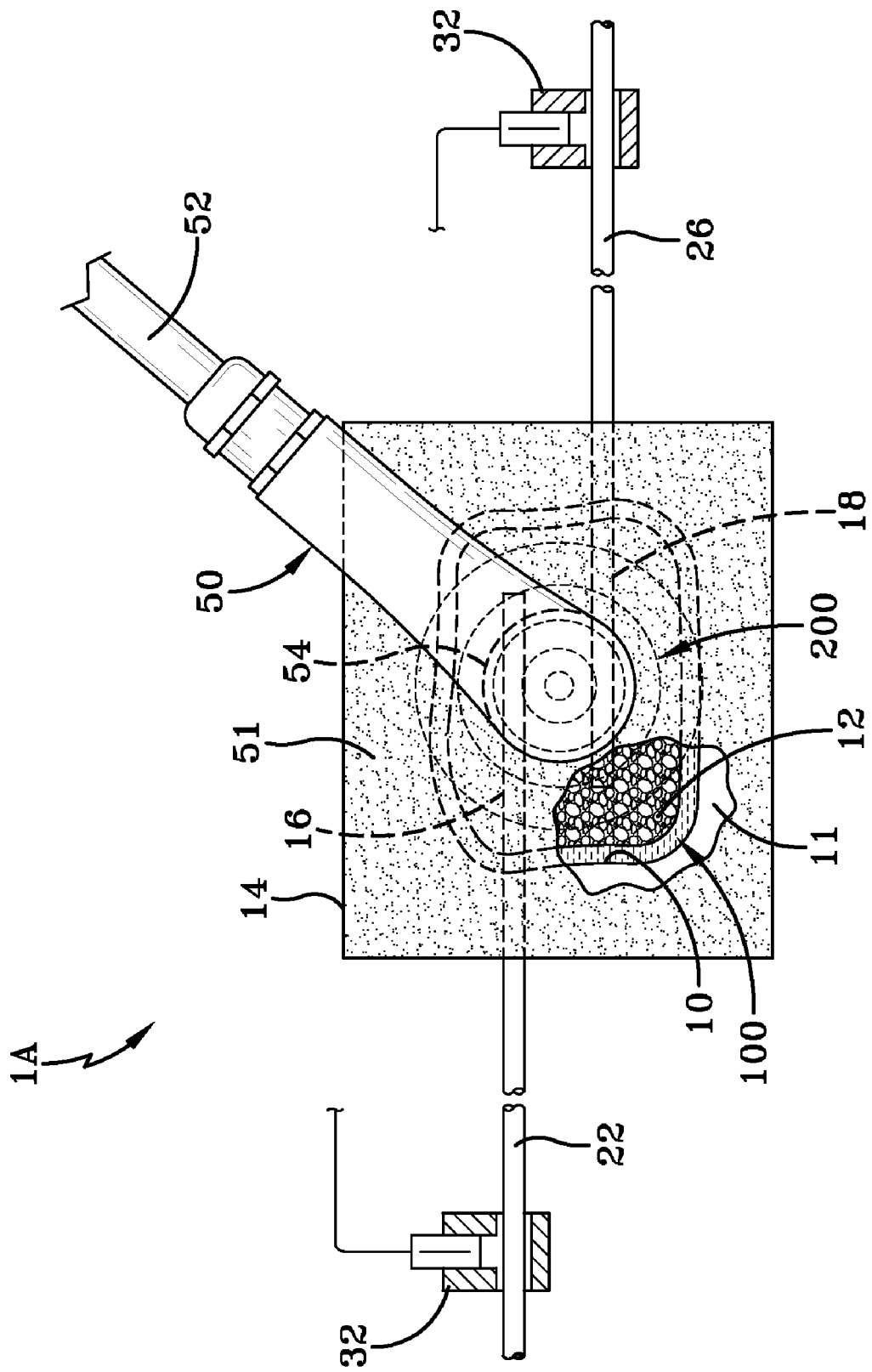
FIG. 4 shows the alternative modified device of FIG. 2 used in combination with a shock wave applicator; the applicator head is illustrated showing how the acoustic shock waves penetrate through the sealing cover into the underlying tissue area.

Now with reference to FIGS. 3 and 4, the above exemplary vacuum bandage device 1 or 1A, can be used in a new and rather unique way in combination with an acoustic shock wave applicator device 50.

With reference to FIGS. 3 and 4, the shock wave applicator 50 connected to a power generating source (not shown) via a connecting a cable 52 can be used in combination with either the wound vacuum bandaging device 1 or 1A or any other bandaging device wherein the porous pad can be completely and totally fluid 100 saturated and wherein any ambient air underlying the foil or sealing cover 14 can be effectively removed. The exemplary devices 1 and 1A provide ideal ways in which fluid 100, either under gravity or otherwise pressurized fluid 100 can be introduced under the sealing foil 14 and prior to the introduction of the fluid 100, a vacuum pulled depresses the sealing cover 14 to compress the porous pad 12 such that as the vacuum is shut off and the supply line is opened the fluid 100 enters and re-saturates the porous pad 12, the entrapped air is evacuated from under the sealing cover 14 through the drainage line and as this is accomplished and all air is removed above the wound area such that the pad 12 and the entire volume area under the sealing cover 14 is completely fluid 100 saturated making it possible to apply acoustic shock wave treatments.

Historically acoustic shock waves were provided using a focusing element that would redirect the waves to converge to a point such that converged waves would have the highest energy at the focal point or focal region of the emitted waves. These acoustic waves had sufficient energy to break up concrements such as kidney stones, however, when used on tissue 11 or bone this could create localized hemorrhaging and a severe introduction of pain. It is well appreciated that the introduction of pain into large, deep wounds is not desirable. It is also well understood that new advances in acoustic shock waves have been achieved whereby tremendous healing potentials can be achieved using unfocused or low energy acoustic shock waves 200 that virtually eliminate the sensation of pain or localized hemorrhaging. With these advances it is now possible to use an acoustic shock wave applicator 50 on a deep wound 10 as described above wherein the acoustic shock waves 200 can be transmitted into the affected tissue 11 without the introduction of pain, but while still providing a germicidal effect and a more rapid healing of the treatment area. Another beneficial feature of using unfocused shock waves 200 is that the transmission occurs over a larger area and therefore the treatment can be accomplished with minimal moving of the applicator 50, therefore the applicator 50 being pressed upon and acoustically coupled to the foil or sealing cover 14 will not cause injurious pain to the patient.

As shown in both FIGS. 3 and 4 an acoustic gel 51 is preferably used to help facilitate the transmission of the acoustic waves 200, as shown the applicator 50 has a side firing head 54 wherein the waves are transmitted in such a fashion that the physician can hold the applicator while the waves are being transmitted onto the treatment surfaces. Alternatively the applicator could be provided with an end firing lens such that the physician would hold the applicator longitudinally and the transmission of waves would occur directly outward from the applicator head. In either case it is desirable that with a wide focused area shock waves be produced at low energy to minimize the sensation of pain and to reduce the convergence to a maximum amplitude that is far less than those found in focused shock waves that use a narrow focal point. Alternatively either planar or divergent or convergent waves wherein the focal point is outside the tissue 11 area or body such that the patient does not require additional anesthesia or numbing of the wound site area.

As shown and as described above, it is preferable that the application of the shock waves 200 occur when the foil or sealing cover 14 is in a distended or slightly outward position as created when the vacuum valve is closed and the fluid supply line is allowed to fill the area with fluid 100 causing a slight distension or ballooning of the cover 14. This bowing of the cover gives evidence that the entire wound area is fluid 100 filled greatly enhancing the ability to transmit the acoustic shock waves 200. Once the acoustic shock waves 200 have been applied the vacuum treatment device can be used as described above wherein during the healing time a slight vacuum can be pulled such that the decomposing tissue 11 and fluid 100s within the wound and bandage are pulled under vacuum allowing sufficient drainage to the wound site area as is currently the practice.

Assuming the entire wound area is within a projected area of the wave transmission, a single transmission 200 dosage of wave energy may be used. The transmission dosage can be from a few seconds to 20 minutes or more dependent on the condition. Preferably the waves are generated from an unfocused or wide area focused source. The unfocused waves can be divergent, planar or near planar and having a low pressure amplitude and density in the range of 0.00001 mJ/mm$^2$ to 1.0 mJ/mm$^2$ or less, most typically below 0.2 mJ/mm$^2$. The focused source preferably can use a diffusing lens or have a far-sight focus to minimize if not eliminate having the localized focus point within the tissue 11. Preferably the focused shock waves are used at a similarly effective low energy transmission or alternatively can be at higher energy but wherein the tissue 11 target site is disposed pre-convergence inward of the geometric focal point of the emitted wave transmission.

These shock wave energy transmissions are effective in stimulating a cellular response and can be accomplished without creating the cavitation bubbles in the tissue 11 of the target site. This effectively insures the tissue 11 or organ does not have to experience the sensation of hemorrhaging so common in the higher energy focused wave forms having a focal point at or within the targeted treatment site.

If the target site or wound is larger than the emitted wave pattern the target site may be such that the patient or the generating source must be reoriented relative to the site and a second, third or more treatment dosage can be administered. The fact that the dosage can be at a low energy the common problem of localized hemorrhaging is reduced making it more practical to administer multiple dosages of waves 200 from various orientations to further optimize the treatment and cellular stimulation of the wound site. Heretofore focused high energy multiple treatments induced pain and discomfort to the patient. The use of low energy focused or un-focused waves at the target site enables multiple sequential treatments.

The present method does not rely on precise site location per se, although can be used in combination with such known devices as ultrasound, cat-scan or x-ray imaging if needed. The physician's general understanding of the anatomy of the patient should be sufficient to locate the target area to be treated. This is particularly true when the wound is within the surgeon's line of sight and this permits the lens or cover of the emitting shock wave applicator 50 to impinge on sealing cover 14 or adjacent tissue 11 directly or through a transmission enhancing gel 51, water or fluid medium during the shock wave treatment. Ideally the foil or sealing cover 14 may be transparent or at least translucent such that any entrapped air bubbles can be observed and removed from under the foil or sealing cover 14 prior to transmitting the shock wave treatment. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue 11 while still providing a stimulating stem cell activation or a cellular release or activation of VEGF and other growth factors.

Due to the wide range of beneficial treatments available it is believed preferable that the optimal use of one or more wave generators or sources should be selected on the basis of the specific application. Wherein relatively small target sites may involve a single wave generator placed on an adjustable manipulator arm. A key advantage of the present inventive methodology is that it is complimentary to conventional medical procedures. In the case of any operative surgical procedure the surgical area of the patient can be bombarded with these low energy waves to stimulate cellular release of healing agents and growth factors. This will dramatically reduce the healing process time. Most preferably such patients may be provided more than one such treatment with an intervening dwell time for cellular relaxation prior to secondary and tertiary post operative or post trauma treatments.

The underlying principle of these shock wave therapy methods is to stimulate the body's own natural healing capability. This is accomplished by deploying shock waves to stimulate strong cells in the tissue 11 to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly not only can the energy intensity be reduced but also the number of applied shock wave impulses can be lowered from several thousand to as few as one or more pulses and still yield a beneficial stimulating response.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue 11 appear to be activated which leads to the remarkable ability of the targeted organ or tissue 11 to generate new growth or to regenerate weakened vascular networks in for example the vascular system. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stem cells can occur within the patients own body activating the naturally occurring stem cells or stem cells that have been introduced to the patient as part of a treatment beneficially utilizing stem cells. This is a significant clinical value in its own right.

This invention further provides germicidal cleaning of diseased or infected areas and for wound cleaning generally after exposure to vacuum wound bandaging devices.

The use of shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

The design of sources with low pressure amplitudes and energy densities. First: spherical waves generated between two tips of an electrode; and second: nearly even waves generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern a planar or a nearly planar wave pattern and can be used in isolation or in combination with focused wave patterns yielding to an improved therapeutic treatment capability that is non-invasive with few if any disadvantageous contraindications. Alternatively a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue 11 trauma while insuring cellular stimulation to enhance the healing process.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factors thereby inducing or accelerating healing.

The unfocused shock waves can be of a divergent wave pattern, planar or near planar pattern preferably of a low peak pressure amplitude and density. Typically the energy density values range as low as $0.000001$ $mJ/mm^2$ and having a high end energy density of below $1.0$ $mJ/mm^2$, preferably $0.20$ $mJ/mm^2$ or less. The peak pressure amplitude of the positive part of the cycle should be above $1.0$ and its duration is below 1-3 microseconds.

The treatment depth can vary from the surface to the full depth of the treated wound. The treatment site can be defined by a much larger treatment area than the $0.10$-$3.0$ $cm^2$ commonly produced by focused waves. The above methodology is particularly well suited for surface as well as sub-surface soft tissue 11 wound treatments.

The above methodology is valuable in generation of new tissue 1, vascularization and may be used in combination with stem cell therapies as well as regeneration of tissue 11 and vascularization.

The methodology is useful in stimulating enforcement of defense mechanisms in tissue 11 cells to fight infections from bacteria and can be used germicidally to treat or cleanse wounds or other target sites which is a primary concern in the case of chemical or radiation burns resulting from such exposures to radiation or chemical agents and burns generally wherein the wound also includes decomposing burned tissue 11.

While the above listed indications cited above are not exhaustive nor intended to be limiting, it is exemplary of the wide range of beneficial uses of low energy and amplitude unfocused divergent, planar or nearly planar shock waves, convergent shock waves, diffused shock waves or a combination of shock wave types in the treatment of humans and other mammals that are exposed to wounds wherein vacuum bandaging devices are employed.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. An acoustic shock wave and vacuum wound treatment device for application to tissue, the device comprising:
   a porous padding for application upon a treatment surface of the tissue;
   an air tight water vapor permeable foil or sealing cover for covering the treatment surface and the porous padding which seals the treatment surface from air;
   at least one fluid supply line for supplying fluid to the treatment surface and the porous pad;

at least one fluid removal line for removing fluid from the treatment surface and the porous padding, the removal line being to a vacuum line, wherein the introduction of fluids through the supply line in combination with the removal of fluids and entrapped air through the removal line thereby fluid saturates the porous pad and treatment surface; and wherein an acoustic shock wave applicator head device being acoustically coupled to either the foil or sealing cover, the foil or sealing cover and adjacent tissue or the adjacent tissue for transmission of acoustic shock waves to the treatment surface through the fluid saturated porous padding, and wherein the transmission of acoustic shock waves are emitted from the shock wave applicator as pressure pulses or acoustic shock waves in a transmission dosage directed toward the treatment surface of the tissue to impinge the tissue of a wound with pressure pulses or shock waves having a low energy density in the range of 0.00001 mJ/mm² to 1.0 mJ/mm²; the pressure pulse being an acoustic pulse which includes several cycles of positive and negative pressure, wherein the pressure pulse has an amplitude of the positive part of such a cycle above 0.1 MPa and the time duration of the pressure pulse is from below a microsecond to a second, rise times of the positive part of the first pressure cycle being in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (μs) for the positive part of a cycle and typically above some micro-seconds for the negative part of a cycle; wherein the transmission dosage subjects the tissue of the wound to convergent, divergent, planar or near planar acoustic shock waves or pressure pulses in the absence of a focal point impinging the substance stimulating a cellular response in the absence of creating cavitation bubbles evidenced by not experiencing the sensation of increased cellular hemorrhaging in the tissue of the wound caused by the emitted waves or pulses in the tissue of the wound wherein the tissue of the wound is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the tissue of the wound or beyond the tissue of the wound thereby passing the emitted waves through the tissue of the wound while avoiding having any localized focal point within the tissue of the wound and wherein the emitted pressure pulses or shock waves are convergent, divergent, planar or near planar and the pressure pulse shock wave is based on electro-hydraulic, electromagnetic, piezoceramic or ballistic wave generation having an energy density value ranging as low as 0.00001 mJ/mm² to a high end of below 1.0 mJ/mm².

2. The acoustic shock wave and vacuum wound treatment device of claim 1 wherein the acoustic shock wave device transmits one of convergent, divergent, near planar or unfocused acoustic shock waves to the treatment surface and underlying tissue.

3. The acoustic shock wave and vacuum wound treatment device of claim 1 wherein said porous padding is comprised of an elastic compressible porous material.

4. The acoustic shock wave and vacuum wound treatment device of claim 3 wherein the porous padding is comprised of an open pored polyvinyl alcohol-sponge foam material.

5. The acoustic shock wave and vacuum wound treatment device of claim 1 further comprises:
   a controller;
   a supply side valve;
   a return side valve;
   a vacuum line connected to the return side valve;
   a supply side fluid pressure infusion line connected to the supply side valve; and
   wherein the controller can actuate the supply side valve, the return side valve, the vacuum line or the pressure infusion line to provide a fluid filled infusion of said porous pad or a drainage of said porous pad and treatment surface or a combination thereof for simultaneous fluid infusion and vacuum drainage.

6. The acoustic shock wave and vacuum wound treatment device of claim 5 wherein after a fluid infusion wherein the return side valve is either closed or restricted there is created a fluid filled reservoir directly under the foil or sealing cover void of air; and wherein an acoustic shock wave treatment is applied through the foil or sealing cover, the tissue adjacent the sealing cover or a combination of the two passing through the fluid saturated porous padding to the treatment tissue and underlying tissue.

7. The acoustic shock wave and vacuum wound treatment device of claim 6 wherein the return side valve can be closed and vacuum applied through the vacuum line to create a sub atmospheric pressure to the treatment tissue which in combination with the administered acoustic shock waves stimulates the tissue to accelerate a rate of healing of the tissue of the wound.

8. A method of treating wounds of tissue comprises the step of:
   applying a porous pad upon a treatment surface of the tissue, covering the treatment surface and porous pad with a sealing cover for isolating the treatment surface and the porous pad from the atmosphere, a space between the sealing cover and treatment surface form a volume;
   filling the volume under the sealing cover with fluid and purging air from the volume under the sealing cover thereby fluid saturating said porous pad;
   applying an acoustic shock wave treatment through the sealing cover or surrounding tissue or a combination thereof sending acoustic shock waves through the volume to the treatment surface and underlying tissue and wherein the transmission of acoustic shock waves are emitted from the shock wave applicator as pressure pulses or acoustic shock waves in a transmission dosage directed toward the treatment surface of the tissue to impinge the tissue of a wound with pressure pulses or shock waves having a low energy density in the range of 0.00001 mJ/mm² to 1.0 mJ/mm²; the pressure pulse being an acoustic pulse which includes several cycles of positive and negative pressure, wherein the pressure pulse has an amplitude of the positive part of such a cycle above 0.1 MPa and the time duration of the pressure pulse is from below a microsecond to a second, rise times of the positive part of the first pressure cycle being in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (μs) for the positive part of a cycle and typically above some micro-seconds for the negative part of a cycle; wherein the transmission dosage subjects the tissue of the wound to convergent, divergent, planar or near planar acoustic shock waves or pressure pulses in the absence of a focal point impinging the substance stimulating a cellular response in the absence of creating cavitation bubbles evidenced by not experiencing the sensation of increased cellular hemorrhaging in the tissue of the wound caused by the emitted waves or pulses in the tissue of the wound wherein the tissue of the wound is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the tissue of the wound or beyond the tissue of the wound thereby passing the emitted waves through the tissue of the wound while avoiding having any localized focal point within the tissue of the wound and wherein the emitted pressure pulses or shock waves are convergent, divergent, planar or near planar and the pressure pulse shock wave is based on electro-hydraulic, electromagnetic, piezoceramic or ballistic wave generation having an energy density value ranging as low as 0.00001 mJ/mm$^2$ to a high end of below 1.0 mJ/mm$^2$;

and pulling a vacuum to create a sub-atmospheric pressure under the sealing cover, wherein the combination of applied acoustic waves and the sub-atmospheric conditions stimulate healing of the treatment surface and underlying tissue.

9. The method of treatment of claim 8 wherein the acoustic shock waves are unfocused or wide area focused shock wave pattern.

10. The method of treatment of claim 9 wherein the shock waves are of a sufficiently low energy or amplitude to avoid the sensation of pain.

11. The method of treatment of claim 9 wherein the treatment of the acoustic shock waves creates a germicidal effect on the porous pad and the treatment surface of the tissue, and a fluid drainage within the volume under the cover removes tissue toxins and other decomposition products.

12. The method of treatment of claim 8 further comprises the step of introducing a medicament antiseptic or antibiotic into the volume under the sealing cover prior to activation of the shock waves to stimulate absorption or covering of the treatment surface tissue during and after the shock wave treatment.

* * * * *